US010952663B2

(12) United States Patent
Nishiyama et al.

(10) Patent No.: US 10,952,663 B2
(45) Date of Patent: Mar. 23, 2021

(54) DEMENTIA INFORMATION OUTPUT SYSTEM AND RECORDING MEDIUM

(71) Applicant: Panasonic Intellectual Property Management Co., Ltd., Osaka (JP)

(72) Inventors: Takashi Nishiyama, Hyogo (JP); Yoshihiro Matsumura, Osaka (JP); Kengo Abe, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 96 days.

(21) Appl. No.: 16/068,117

(22) PCT Filed: Mar. 6, 2017

(86) PCT No.: PCT/JP2017/008657
§ 371 (c)(1),
(2) Date: Jul. 4, 2018

(87) PCT Pub. No.: WO2017/154805
PCT Pub. Date: Sep. 14, 2017

(65) Prior Publication Data
US 2019/0231246 A1     Aug. 1, 2019

(30) Foreign Application Priority Data
Mar. 9, 2016   (JP) .............................. JP2016-046358

(51) Int. Cl.
*A61B 5/11* (2006.01)
*A61B 5/00* (2006.01)
(Continued)

(52) U.S. Cl.
CPC .............. *A61B 5/4088* (2013.01); *A61B 5/11* (2013.01); *A61B 5/1118* (2013.01); *A61B 10/00* (2013.01)

(58) Field of Classification Search
CPC ........... A61B 5/11; A61B 5/00; A61B 5/0205; A61B 5/02055; A61B 5/4812;
(Continued)

(56) References Cited

U.S. PATENT DOCUMENTS

| 9,192,333 B1 * | 11/2015 | Hayes ................. A61B 5/7264 |
| 2014/0074180 A1 * | 3/2014 | Heldman ........... A61N 1/36139 607/45 |
| 2015/0257696 A1 | 9/2015 | Yamaguchi |

FOREIGN PATENT DOCUMENTS

| JP | 2005-287641 | 10/2005 |
| JP | 2005-304941 | 11/2005 |

(Continued)

OTHER PUBLICATIONS

International Search Report (ISR) dated Apr. 4, 2017 in International (PCT) Application No. PCT/JP2017/008657.

*Primary Examiner* — Jon Eric C Morales
(74) *Attorney, Agent, or Firm* — Renner, Otto, Boisselle & Sklar, LLP

(57) ABSTRACT

A dementia determination device in a dementia information output system includes an obtainer which obtains, on a per unit period basis, the result of measuring body motion of a user in a sleep time period; and an outputter which outputs dementia information indicating the likelihood that the user is developing a mild cognitive disorder based on the occurrence frequency of a unit period in which the magnitude of a difference between reference data on body motion of a healthy subject in a sleep time period and the result of measuring obtained by the obtainer exceeds a predetermined threshold value.

11 Claims, 12 Drawing Sheets

(51) Int. Cl.
*A61N 1/372* (2006.01)
*A61N 1/36* (2006.01)
*A61B 10/00* (2006.01)

(58) Field of Classification Search
CPC ............... A61B 5/4082; A61B 5/4836; A61N 1/36082; A61N 1/3606
USPC .............................. 600/301, 483, 484, 595
See application file for complete search history.

(56) References Cited

FOREIGN PATENT DOCUMENTS

| | | |
|---|---|---|
| JP | 2007-282992 | 11/2007 |
| JP | 2014-018341 | 2/2014 |
| JP | 2015-138488 | 7/2015 |
| WO | 2014/013999 | 1/2014 |

\* cited by examiner

DEMENTIA INFORMATION OUTPUT SYSTEM AND RECORDING MEDIUM

TECHNICAL FIELD

The present invention relates to a dementia information output system which, for example, determines dementia and a non-transitory recording medium having recorded thereon a control program which is used by a device included in the dementia information output system.

BACKGROUND ART

Conventionally, a system for discerning early-stage dementia is known which discerns dementia by finding an operation different from a regular tendency on the basis of the operating status of a switch on a terminal (refer to Patent Literature (PTL) 1).

CITATION LIST

Patent Literature

PTL 1: Japanese Unexamined Patent Application Publication No. 2014-018341

SUMMARY OF THE INVENTION

Technical Problem

The system for discerning early-stage dementia disclosed in PTL 1 sets a rule that a subject must operate the switch upon awakening every day and determines, according to whether or not the subject forgets to operate the switch, whether or not the subject has dementia.

An object of the present invention is to provide a dementia information output system capable of outputting dementia information indicating the likelihood of development of a mild cognitive disorder without the need to set a rule such as a switch operation. Another object of the present invention is to provide a non-transitory recording medium having recorded thereon a control program (a program for computers) used in the dementia information output system. Note that the term "mild cognitive disorder" is used herein to refer to the concept encompassing mild dementia and mild cognitive impairment (MCI) which precedes dementia. The mild cognitive disorder is distinguished from the state of being healthy and normal.

Solutions to Problem

In order to achieve the aforementioned object, a dementia information output system according to an aspect of the present invention includes: an obtainer which obtains, on a per unit period basis, a result of measuring body motion of a user in a sleep time period; and an outputter which outputs dementia information indicating a likelihood that the user is developing a mild cognitive disorder, the likelihood being based on an occurrence frequency of a unit period in which a magnitude of a difference between reference data on body motion of a healthy subject in a sleep time period and the result of measuring obtained by the obtainer exceeds a predetermined threshold value.

Furthermore, a non-transitory recording medium having the a control program recorded thereon according to an aspect of the present invention is for causing a device including a microprocessor to execute a dementia information output process including: obtaining, on a per unit period basis, a result of measuring body motion of a user in a sleep time period; and outputting dementia information indicating a likelihood that the user is developing a mild cognitive disorder based on an occurrence frequency of a unit period in which a magnitude of a difference between reference data on body motion of a healthy subject in a sleep time period and the result of measuring obtained exceeds a predetermined threshold value.

Advantageous Effect of Invention

With the present invention, it is possible to obtain dementia information indicating the likelihood of development of a mild cognitive disorder without the need for rules such as a switch operation.

DESCRIPTION OF EXEMPLARY EMBODIMENTS

Underlying Knowledge of Invention

It is known that a sleep disorder such as light sleep is a symptom of dementia. Dementia is considered to be associated with a wide and severe organic brain disorder over the hypothalamus and the brainstem which control the biological clock for sleeping, awakening, etc. For example, patients with Alzheimer-type dementia are known to frequently repeat the sleep-wake cycle in the period from sleep onset at night to time of awakening next morning (sleep time period).

On the basis of this knowledge, the inventors of the present invention conducted experiments and found that the measurement result (the amount of body motion) from a body motion sensor in the sleep time period of the elderly is different between the case in which the elderly is healthy and normal and the case in which the elderly develops a mild cognitive disorder.

Figure 1A:
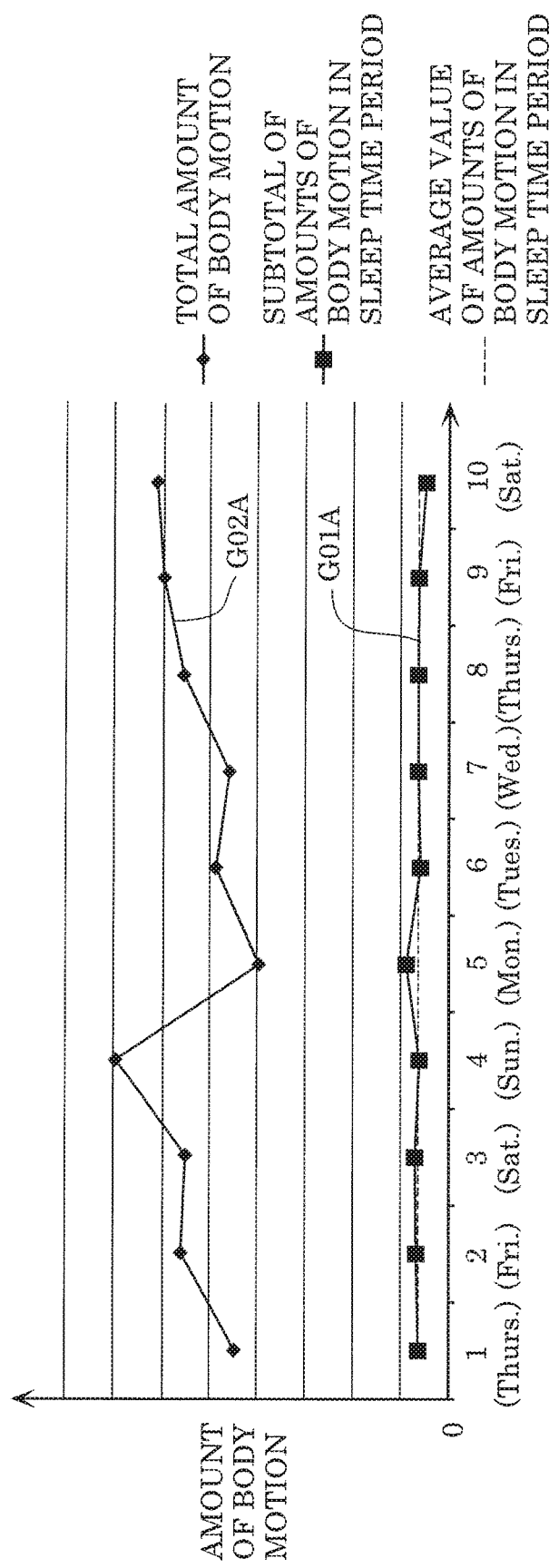
FIG. 1A is a graph visualizing transitions in an amount of body motion in a sleep time period of a healthy subject (a person in the state of being healthy and normal).
Figure 1B:
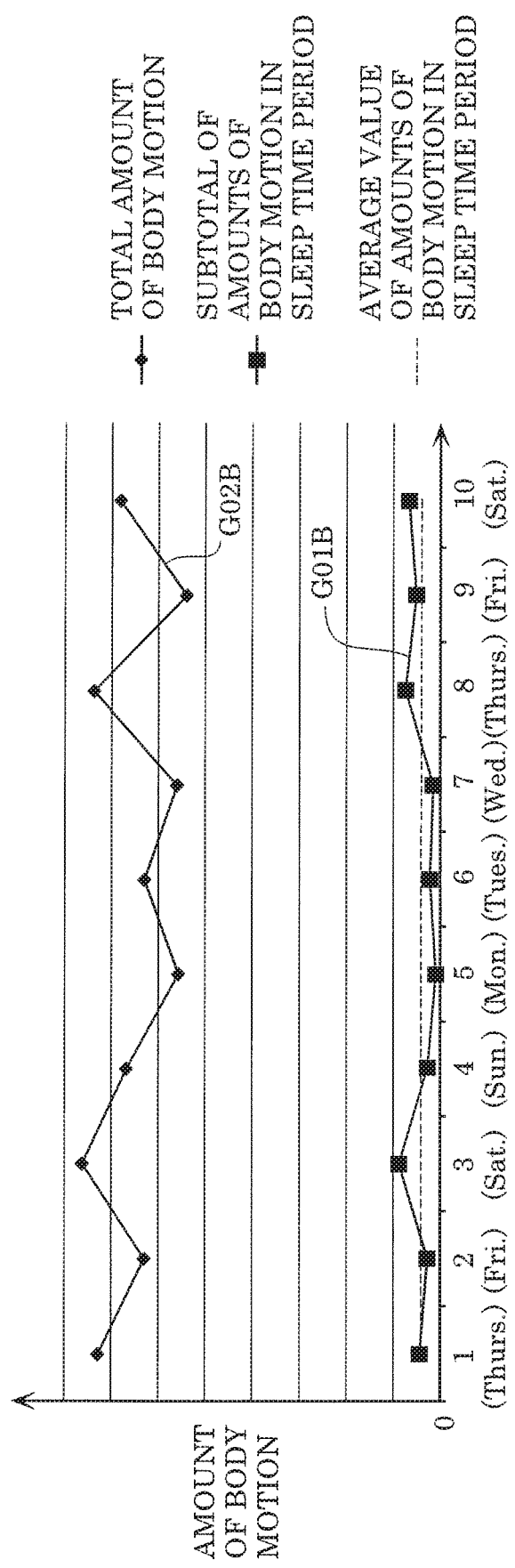
FIG. 1B is a graph visualizing transitions in an amount of body motion in a sleep time period of a patient with a mild cognitive disorder.

FIG. 1A illustrates graph G01A of the transition in the amount of body motion in the sleep time period of a healthy elderly subject (a person in the state of being healthy and normal), and FIG. 1B illustrates graph G01B of the transition in the amount of body motion in the sleep time period of an elderly patient with dementia. FIG. 1A and FIG. 1B schematically visualize the results of the experiment. In this example, the sleep time period is defined as a fixed period between 23 o'clock and 6 o'clock. FIG. 1A and FIG. 1B further show graphs G02A and G02B of transitions of the total amount of body motion of one day including the sleep time period. The amount of body motion in the sleep time period in this example is accumulation of per-minute measurement values of body motion, which are any of ten different values from 0 (the minimum value such as no body motion) to 9 (the maximum value), from a body motion sensor in the sleep time period. The total amount of body motion of one day in this example is accumulation of per-minute measurement values of body motion, which are any of ten different values from 0 (the minimum value such as no body motion) to 9 (the maximum value), from the body motion sensor in one day (24 hours).

As illustrated in FIG. 1A, the total amount of body motion of the healthy subject varies somewhat significantly each day, but the amount of body motion of the healthy subject in the sleep time period does not vary much. In contrast, as shown in graph G01B in FIG. 1B, the per-day (per-24-hour) change in the amount of body motion of the patient with dementia in the sleep time period is greater than that in the amount of body motion of the healthy subject in the sleep time period shown by graph G01A in FIG. 1A. Note that as shown in graph G02B in FIG. 1B, the total amount of body motion of the patient with dementia varies somewhat significantly each day, similar to the total amount of body motion of the healthy subject shown in graph G02A in FIG. 1A. Thus, paying attention to the body motion in the sleep time period is useful for distinguishing patients with dementia and healthy subjects. Since the patient is healthy and normal before developing the dementia, measuring the body motion in the sleep time period is useful for making a distinction between before and after the development of a mild cognitive disorder (in other words, the distinction between the state of being healthy and normal and the state of a mild cognitive disorder).

According to the above knowledge and so on, the technical concept of a dementia information output system capable of outputting dementia information indicating the likelihood of development of a mild cognitive disorder on the basis of the result of measuring body motion in a sleep time period has been created. Hereinafter, embodiments of the dementia information output system will be described with reference to the drawings. Each of the embodiments herein shows a specific example of the present invention. Thus, the numerical values, shapes, materials, structural elements, and the arrangement and connection of the structural elements, steps, the processing order of the steps, etc., shown in the following embodiments are mere examples, and are not intended to limit the present invention. Among the structural elements in the following embodiments, structural elements not recited in independent claims can be arbitrarily included. The figures are schematic diagrams and are not necessarily precise illustrations.

Embodiment 1

Dementia information output system 10 according to an embodiment of the present invention will be described below.

Configuration

Dementia information output system 10 measures the body motion of a subject (user) such as the elderly or the person in need of assistance by a body motion sensor, determines whether or not the user is developing the mild cognitive disorder, and outputs dementia information indicating the likelihood of development of the mild cognitive disorder (for example, whether or not user is developing the mild cognitive disorder).

Figure 2:
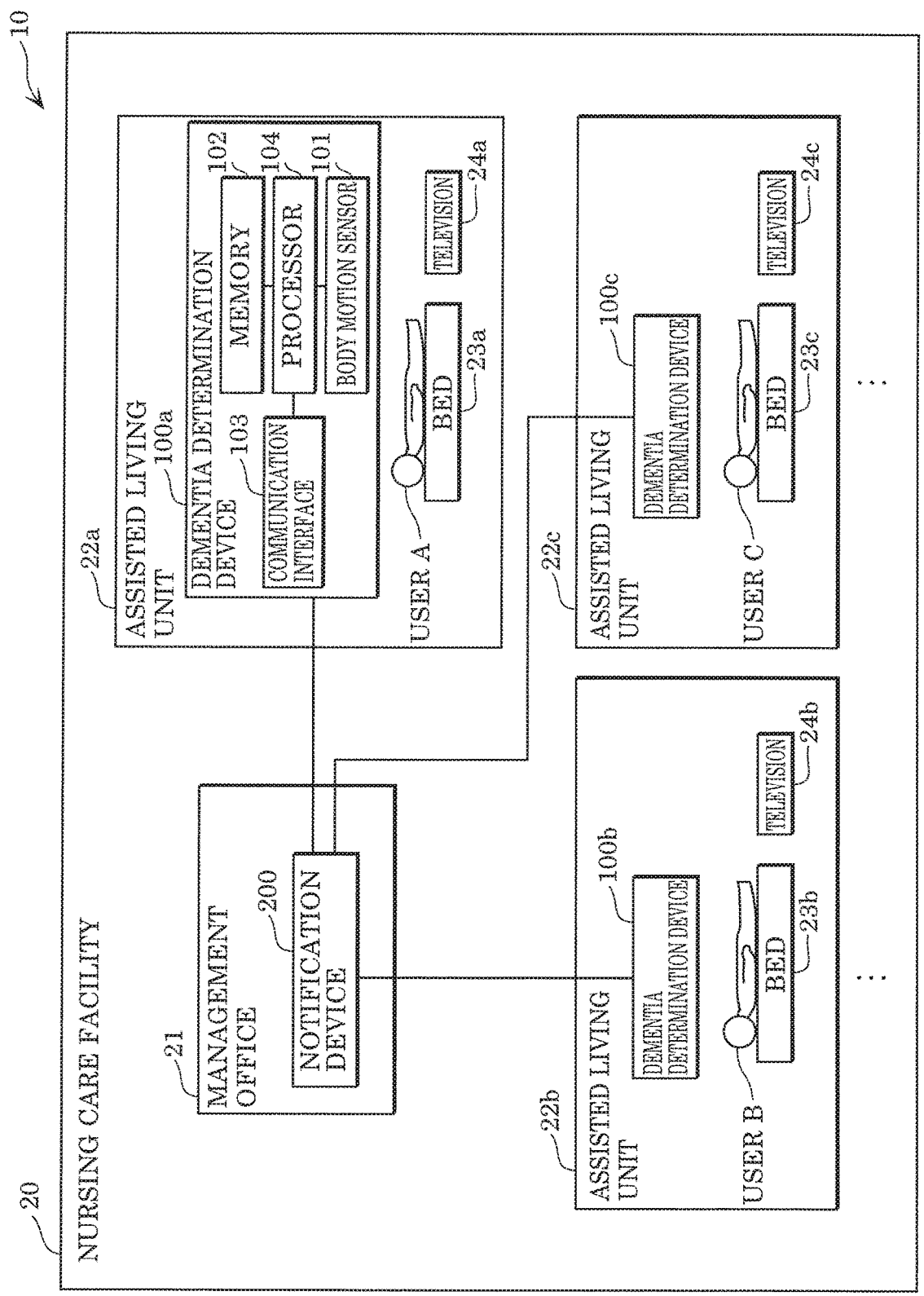
FIG. 2 is a schematic configuration view illustrating an example of a configuration of a dementia information output system according to Embodiment 1.

FIG. 2 is a schematic configuration view illustrating an example of a configuration of dementia information output system 10 according to Embodiment 1. As illustrated in this figure, dementia information output system 10 includes dementia determination devices 100a to 100c and notification device 200. Although three dementia determination devices 100a to 100c are illustrated herein for convenience, dementia information output system 10 may include any number of dementia determination devices which is not less than one.

FIG. 2 illustrates, as an example, dementia information output system 10 applied to nursing care facility (long-term care facility) 20 such as an aged care facility and a convalescent care facility. In dementia information output system 10, dementia determination devices 100a to 100c determine whether or not users A to C living in assisted living units 22a to 22c of nursing care facility 20 are developing the mild cognitive disorder, and sends dementia information indicating the determination results, etc., to notification device 200. Notification device 200 is installed, for example, in management office 21 in which a caretaker such as a care worker, a nurse, a doctor, or the like is mainly present. The caretaker or the like can easily grasp the dementia information about users A to C living in respective assisted living units 22a to 22c (the information about the likelihood that the user may be developing the mild cognitive disorder) by notification device 200 and can appropriately provide necessary treatment, etc.

Assisted living unit 22a is a room which includes bed 23a, television 24a, and the like and in which user A lives; dementia determination device 100a is installed in assisted living unit 22a. Likewise, assisted living units 22b and 22c are rooms which include beds 23a and 23c, televisions 24b and 24c, dementia determination devices 100b and 100c, and the like and in which users B and C live, respectively.

Dementia determination device 100a is an information processing device (computer) that has functions of measuring the body motion of user A by body motion sensor 101, determining, on the basis of the measurement result (the amount of body motion), for example, whether or not user A has the mild cognitive disorder, and transmitting dementia information including the determination result. Dementia determination device 100a includes body motion sensor 101, memory 102, communication interface (I/F) 103, and processor (microprocessor) 104. Although the description herein mainly focuses on dementia determination device 100a installed in assisted living unit 22a for user A, dementia determination devices 100b and 100c also have substantially the same configurations as dementia determination device 100a.

Body motion sensor 101 may be any sensor for sensing the body motion of user A. For example, body motion sensor 101 is a radio-frequency sensor including a transmission and reception circuit that sends (transmits) radio waves (for example, microwaves) and receives reflected waves in order to measure the motion of human bodies. In order to measure the body motion of user A in the sleep time period, body motion sensor 101 is installed, for example, on bed 23a (for example, a part of the bottom located under a mattress) or a ceiling part above bed 23a in assisted living unit 22a.

Memory 102 is, for example, read-only memory (ROM) in which a program and data are held in advance or random-access memory (RAM) which is used to save data and the like upon execution of a program. Memory 102 may include non-volatile memory, for example.

Communication I/F 103 is a communication circuit for communicating with notification device 200. The communication between dementia determination device 100a and notification device 200 may be wireless communication or may be wired communication.

Processor 104 performs a process of controlling communication I/F 103 and the like by executing a control program stored in memory 102. Note that dementia determination device 100a may include, for example, a display such as a liquid-crystal display (LCD), and may display the dementia information on the display.

Notification device 200 installed in management office 21 is a monitoring device including a communication interface and a display, and may be a computer terminal including memory and a processor, for example.

Figure 3:
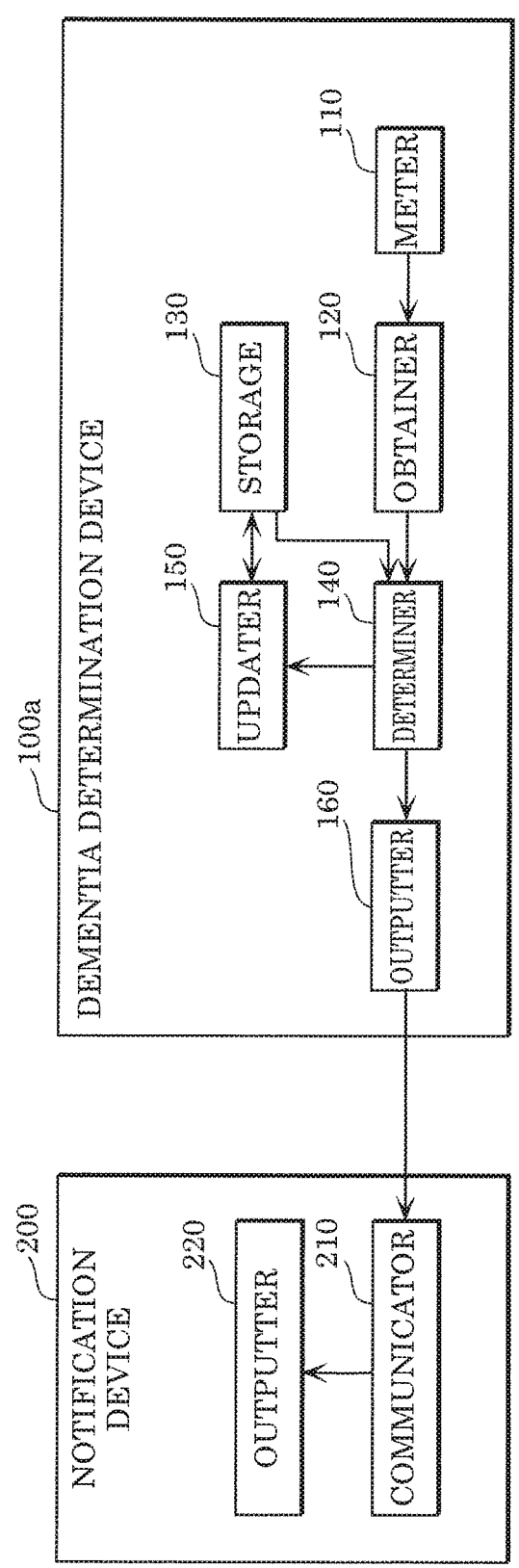
FIG. 3 is a function block diagram of a dementia determination device, etc., according to Embodiment 1.

FIG. 3 is a function block diagram of dementia determination device 100a in dementia information output system 10 according to the present embodiment. Dementia determination device 100a is installed in assisted living unit 22a in which user A lives. In this figure, the functional configuration of notification device 200 installed in management office 21 is also illustrated.

Figure 4:
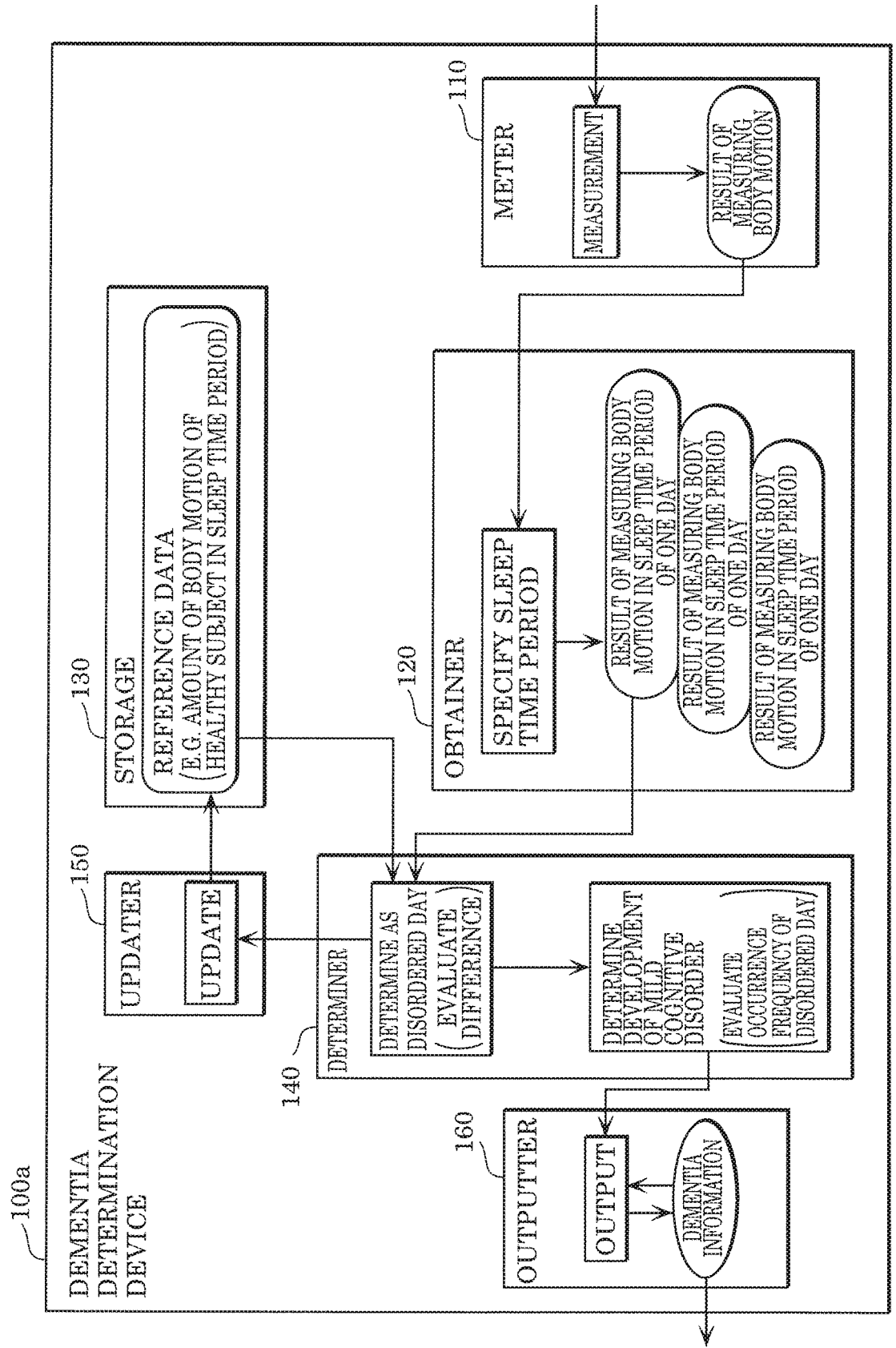
FIG. 4 illustrates the association between functional elements of a dementia determination device according to Embodiment 1.

Dementia determination device 100a including the hardware configuration described above includes, as functional elements, meter 110, obtainer 120, storage 130, determiner 140, updater 150, and outputter 160, as illustrated in FIG. 3, in order to provide the function of outputting the dementia information on the basis of the result of measuring the body motion of user A. FIG. 4 illustrates main processing details and handling information (data) for the functional elements of dementia determination device 100a.

Meter 110 is implemented, for example, by body motion sensor 101 and processor 104 which performs the control program, and has a function of measuring the body motion of user A using body motion sensor 101. For example, in the case where body motion sensor 101 is a radio-frequency sensor, meter 110 identifies the body motion of user A from the waveform of a transmission signal on radio waves sent from the radio-frequency sensor and the waveform of a reception signal on reflected waves, and thus obtains the result of measuring the body motion. With the well-known technique based on the Doppler principle, a frequency (Doppler frequency) proportional to the speed at which a human body, etc., that has reflected the radio waves of the transmission signal moves can be obtained from the difference between the waveform of the transmission signal and the waveform of the reception signal, and the amplitude of the waveform of the Doppler frequency can be obtained. For example, it is possible to specify the result of measuring the body motion (the amount of body motion) according to the amplitude of the waveform obtained when the Doppler frequency obtained using the radio-frequency sensor exceeds a threshold value (for example, 2 Hz) that distinguishes micro vibration (breathing, heartbeat, etc.) and the body motion in the movement of human bodies from each other. Using body motion sensor 101, for example, meter 110 is capable of specifying, on a per-minute basis, the result of measuring the body motion (the amount of body motion) that is a degree of body motion expressed using ten different values from 0 (the minimum value such as no body motion) to 9 (the maximum value).

Obtainer 120 is implemented, for example, by processor 104 which executes the control program, and has a function of obtaining, on a per-unit-period (for example, 24 hours) basis, the result of measuring the body motion of user A in the sleep time period. The description herein assumes that the unit period is 24 hours (one day). Note that when the unit period is 24 hours (one day), the unit period (one day) does not always need to end or start at 0 o'clock AM, and may end or start at noon, for example.

Figure 5:
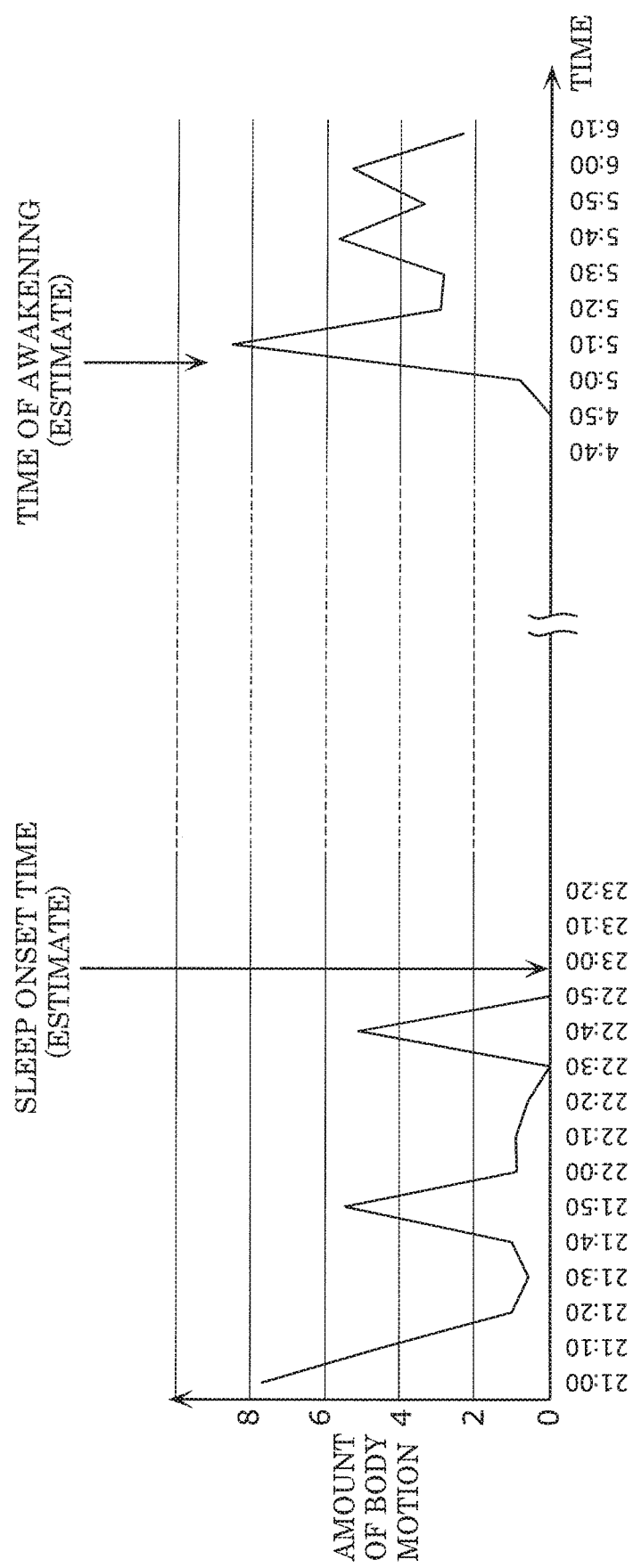
FIG. 5 is a graph illustrating exemplary temporal changes in the result of measuring body motion (an amount of body motion).

Obtainer 120 specifies the sleep time period of user A on the basis of the result of measuring the body motion of user A which is obtained by meter 110, and obtains (specifies) the measurement result in the specified sleep time period. The sleep time period is generally a period of time during sleep, and includes time in the state of being asleep and may include time in the state of being temporarily not asleep (the state of being temporarily awake during the night). One example of the method for specifying the sleep time period is to estimate sleep onset time and time of awakening from the result of measuring the body motion of user A and specify the period of time between the sleep onset time and the time of awakening as the sleep time period. For example, obtainer 120 estimates the sleep onset time from the fact that the state in which the result of measuring the body motion (the amount of body motion) of the user per minute has a value of 0 has continued for a predetermined period of time (for example, a few tens of minutes). Furthermore, obtainer 120 estimates the time of awakening, for example, from the fact that, after the sleep onset time, the state in which the result of measuring the body motion per minute has a value greater than a predetermined value (for example, 1) has continued for a predetermined period of time (for example, a few tens of minutes). FIG. 5 illustrates exemplary temporal changes in the result of measuring the body motion (the amount of body motion). In the example of changes in the amount of body motion schematically illustrated in this figure, 23 o'clock is estimated as the sleep onset time, for example, and 5 o'clock is estimated as the time of awakening, for example. Accordingly, the sleep time period of user A on this day is specified as 23 o'clock to 5 o'clock. Thus, specifying the sleep time period on the basis of the result of measuring the body motion is useful for increasing the accuracy of the determination on the mild cognitive disorder using the result of measuring the body motion of user A in the sleep time period. It is also possible to use a method in which night-time is included in the conditions for estimating the sleep onset time and morning is included in the conditions for estimating the time of awakening, for example. The sleep time period may be specified each day, may be specified at an interval of two or more days, and may be specified only once. Obtainer 120 uses the specified sleep time period to obtain (specify) the result of measuring the body motion of user A in the sleep time period on one day (in a unit period of 24 hours) and transmit the result to determiner 140. The period from a predetermined point in time in the night (for example, 23 o'clock) to a predetermined point in time in the morning (for example, 6 o'clock) may be fixedly specified as the sleep time period.

Storage 130 is implemented, for example, by one region of memory 102, and has a function of storing reference data on the body motion of a healthy subject in the sleep time period which is used for comparison with the result of measuring the body motion of user A in the sleep time period. This healthy subject is, for example, an elderly person who does not have the mild cognitive disorder and may be a healthy person different from user A or may be, for example, user A at the time when the user does not have the mild cognitive disorder. The reference data is to be compared with the result of measuring the body motion of user A in the sleep time period which is obtained by obtainer 120, and thus is useful if it relates to the amount of body motion of user A in the sleep time period measured at the time when the user does not have the mild cognitive disorder. The reference data storage in storage 130 is, for example, the average value of the amounts of body motion of the healthy subject in the sleep time period measured in more than one unit period (more than one day).

Figure 6:
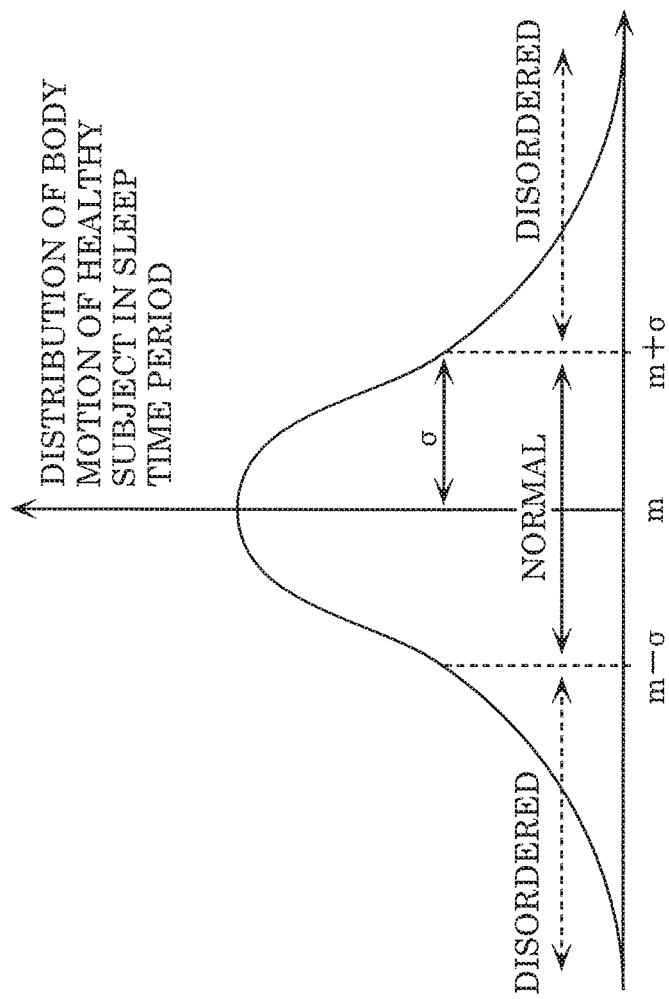
FIG. 6 illustrates the relationship between the distribution of amounts of body motion in a sleep time period of a healthy subject and threshold value $\sigma$ for determining a disordered day.

Determiner 140 is implemented, for example, by processor 104 which executes the control program. Determiner 140 has a disordered day determination function of determining, by comparing the reference data stored in storage 130 and the result of measuring the body motion of user A in the sleep time period of one day which is obtained by obtainer 120 and evaluating the difference (the magnitude of the difference) therebetween, whether the day is a disordered day (a day when the user is not normal) or a normal day (a day when the user is normal). The difference (the magnitude of the difference) to be evaluated by the disordered day determination function is, for example, a ratio or magnitude (absolute value) of difference between the reference data and the result of measuring the body motion of user A in the sleep time period of one day. The description herein assumes that the magnitude of the difference is the absolute value of the difference. For example, when the absolute value of the difference between the reference data and the result of measuring the body motion of user A in one day which is obtained by obtainer 120 exceeds a predetermined threshold value (threshold value σ), determiner 140 determines, as the disordered day determination function, that the day is a disordered day. Furthermore, when the absolute value of the difference does not exceed threshold value σ, determiner 140 determines that the day is a normal day. Here, since the reference data stored in storage 130 is the average value of the amounts of body motion of a healthy subject in the sleep time period measured on more than one day, standard deviation σ of the amounts of body motion measured on the more than one day is used as threshold value σ. FIG. 6 illustrates the relationship between the distribution of amounts of body motion in the sleep time period of a healthy subject and threshold value σ for determining a disordered day. The reference data corresponds to average value m of the distribution of the amounts of body motion in FIG. 6, and when the result of measuring the body motion of user A in the sleep time period is greater than average value m+standard deviation σ and when the result of measuring the body motion of user A in the sleep timer period is less than average value m−standard deviation σ, the day is determined as a disordered day. Note that the predetermined threshold value to be compared with the absolute value of the above-described difference does not always need to be the standard deviation of the amounts of body motion of a healthy subject in the sleep time period measured on more than one day and may be a value obtained by multiplying the standard deviation by a prescribed ratio.

Figure 7:
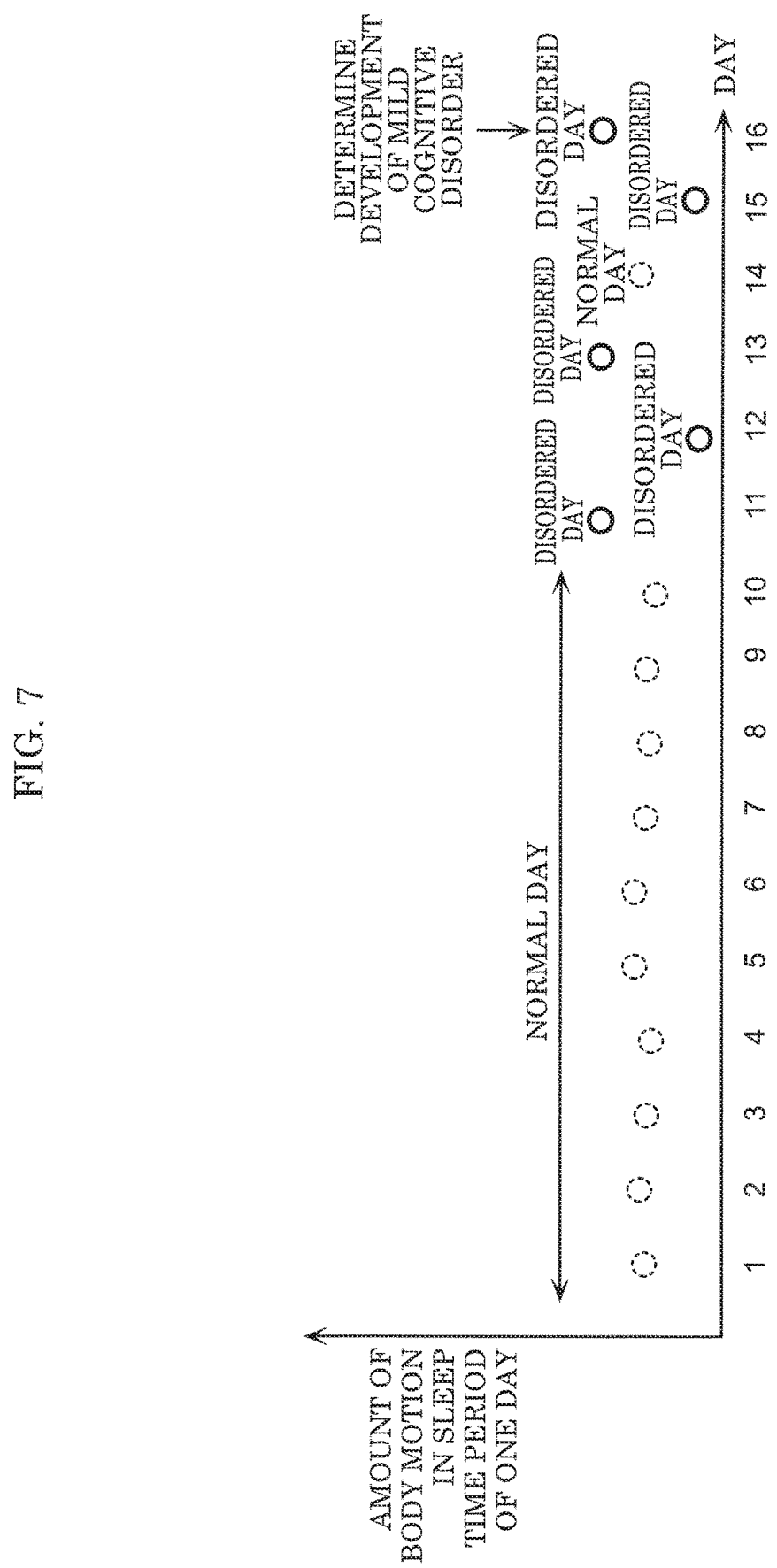
FIG. 7 illustrates an example of the result of determining whether each day is a normal or disordered day.

Determiner 140 further has a mild dementia etc., development determination function of determining development of the mild cognitive disorder by evaluating the occurrence frequency of a unit period in which the magnitude of the difference between the reference data and the result of measuring the body motion of user A in the sleep time period exceeds the predetermined threshold value (threshold value σ) (in other words, the disordered day determined by the disordered day determination function). When the occurrence frequency of the disordered day exceeds a predetermined reference frequency, determiner 140 determines that user A is developing the mild cognitive disorder. The predetermined reference frequency is, for example, a frequency of five days in one week, a frequency of 70% of a period not less than one week, or a frequency of five consecutive days (in other words, a frequency of 100% of a period not less than five days). The occurrence frequency of the disordered day is, for example, an occurrence frequency in prescribed period T more than one week, and in order to more accurately determine whether or not the user is developing the mild cognitive disorder, it is useful that prescribed period T is long (for example, three months). FIG. 7 illustrates an example of the amount of body motion in the sleep time period on each day and the result of determining whether each day is a normal or disordered day. For example, assuming that the predetermined reference frequency is a frequency of 70% in a period not less than the past one week, the occurrence frequency of the disordered day exceeds the predetermined reference frequency on day 16 in the example in FIG. 7; then, determiner 140 determines that user A is developing the mild cognitive disorder.

Updater 150 is implemented, for example, by processor 104 which executes the control program. Updater 150 has a function of updating the reference data so as to reflect the result measured on the day (in the unit period) when the magnitude of the difference between the reference data and the measurement result (the amount of body motion of the user A in the sleep time period) obtained by obtainer 120 does not exceed the predetermined threshold value (threshold value σ). For example, in the case where the reference data is the average value (a value obtained by dividing the total by the number of days) of the amounts of body motion of a healthy subject in the sleep time period measured on more than one day (the total of the amounts of body motion on more than one day), updater 150 can update the reference data as follows. In other words, updater 150 sets, as new reference data (updated reference data), an average value calculated after adding, to the total of the amounts of body motion on more than one day, one day data that is the amount of body motion of user A in the sleep time period on the day determined by determiner 140 as a normal day. Upon this update, for example, threshold value σ which determiner 140 uses to determine whether each day is a normal or disordered day may be updated so as to correspond to the standard deviation of the amounts of body motion on more than one day including the amount of body motion of user A in the sleep time period on the day determined as a normal day. Note that after updater 150 updates the reference data stored in storage 130, determiner 140 makes determination using the updated reference data. In other words, when the occurrence frequency of the disordered day in which the magnitude of the difference between the updated reference data and the measurement result (the amount of body motion of user A in the sleep time period) obtained by obtainer 120 after the update exceeds the predetermined threshold value exceeds the predetermined reference frequency, determiner 140 determines that user A is developing the mild cognitive disorder.

Outputter 160 is implemented, for example, by processor 104 which executes the control program and communication I/F 103. Outputter 160 has a function of outputting dementia information indicating the likelihood that user A may be developing the mild cognitive disorder based on the occurrence frequency of the day (unit period) in which the magnitude of the difference between the reference data stored in storage 130 and the measurement result obtained by obtainer 120 exceeds the predetermined threshold value (threshold value σ). This dementia information indicates that user A is developing the mild cognitive disorder when determiner 140 determines that user A is developing the mild cognitive disorder. Aside from this, outputter 160 may include, in the dementia information, information indicating each disordered day in the past prescribed period, information indicating the number of disordered days, and information indicating a transition of the amount of body motion of user A in the sleep time period in the past prescribed period, for example. Note that outputter 160 may be configured not to output the dementia information when determiner 140 does not determine that user A is developing the mild cognitive disorder. Furthermore, when determiner 140 does not determine that user A is developing the mild cognitive disorder, outputter 160 may output dementia information including an index value (the unit of which is percent, for example) of the occurrence frequency, etc., of disordered days (a degree, etc., indicating a suspicion of the mild cognitive disorder) in the past prescribed period. Outputter 160 outputs the dementia information by transmitting the dementia information to notification device 200. In notification device 200, outputter 220 displays dementia information on a display on the basis of the dementia information received by communicator 210. Furthermore, in the case where dementia determination device 100a includes a display, outputter 160 of dementia determination device 100a may output the dementia information by displaying the dementia information on the display.

Operations

Operations of dementia determination device 100a in dementia information output system 10 including the above-described configuration will be described below.

Figure 8:
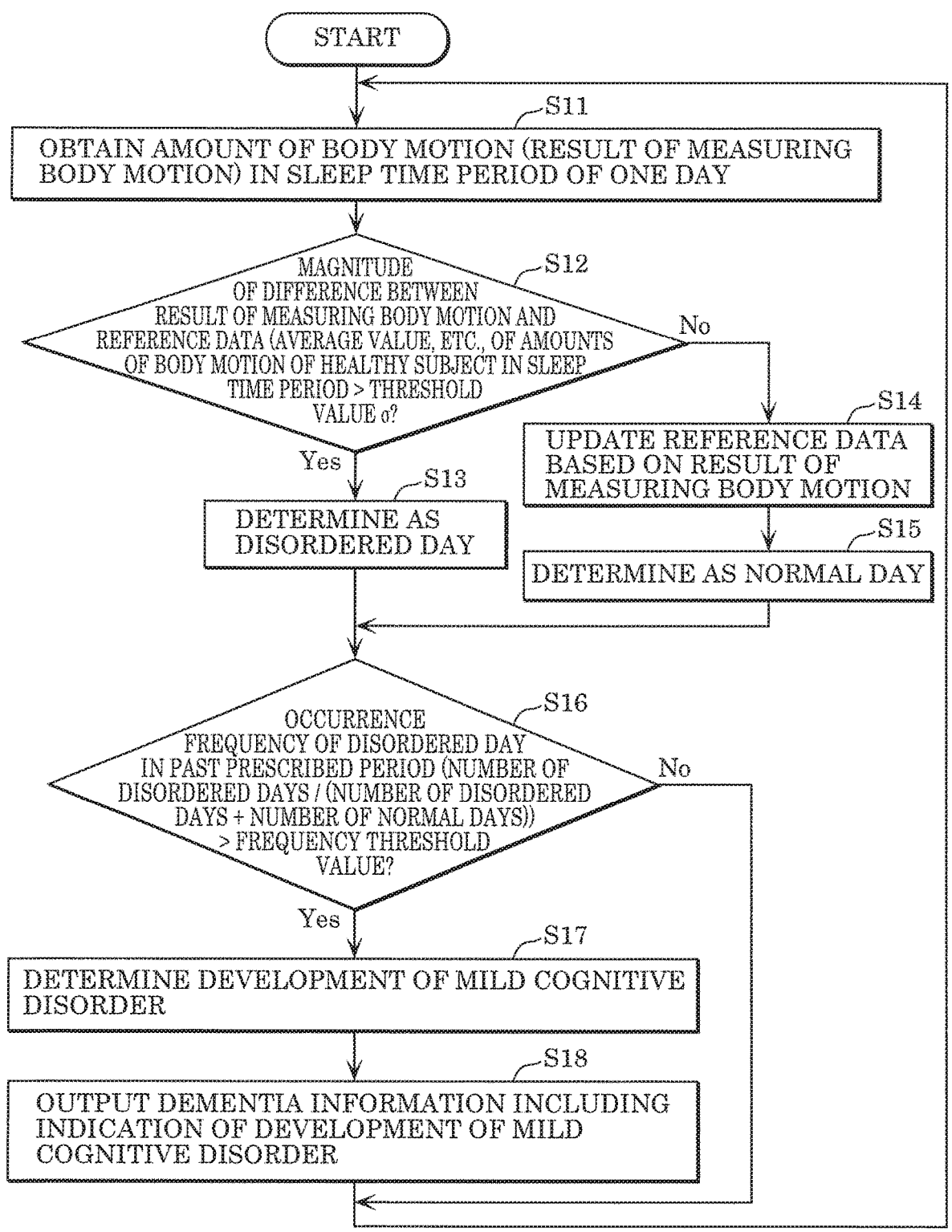
FIG. 8 is a flowchart illustrating a dementia information output process in a dementia determination device according to Embodiment 1.

FIG. 8 is a flowchart illustrating a dementia information output process in dementia determination device 100 according to the present embodiment. The dementia information output process will be described below with reference to this figure.

Dementia determination device 100a measures the body motion of user A by meter 110 using body motion sensor 101 and obtains the result of measuring the body motion (the amount of body motion) in the sleep time period of one day by obtainer 120 (Step S11).

Determiner 140 in dementia determination device 100a discerns whether or not the magnitude of the difference between the result of measuring the body motion of user A in the sleep time period of one day which is obtained in Step S11 and the reference data stored in storage 130 exceeds threshold value σ (Step S12). The reference data to be used for discerning in Step S12 is, for example, the average value of the amounts of body motion of a healthy subject in the sleep time period, and may be, for example, the average value of the amounts of body motion of user A in the sleep time period that is measured at the time when user A is healthy and normal. In Step S12, when the magnitude of the difference between the measurement result and the reference data exceeds threshold value σ, determiner 140 determines that the day is a disordered day (Step S13). When the magnitude of the difference between the result of measuring the body motion in the sleep time period of one day and the reference data does not exceed threshold value σ, determiner 140 causes updater 150 to update the reference data on the basis of the result of measuring the body motion (Step S14), and determines that the day is a normal day (Step S15).

Subsequently, determiner 140 discerns whether or not the occurrence frequency of the disordered day in the past prescribed period exceeds the frequency threshold value (predetermined reference frequency) (Step S16). This past prescribed period is, for example, one week, and, for example, the period from the first disordered day to the present may be set as the past prescribed period. When the occurrence frequency of the disordered day exceeds the predetermined reference frequency in Step S16, determiner 140 determines that user A is developing the mild cognitive disorder (Step S17). By using the occurrence frequency of the disordered day, it is possible to reduce the possibility of erroneous determination as developing the mild cognitive disorder, for example, in the case where there is a day when the body motion becomes great with discomfort due to heat in the sleep time period on a sweltering summer night, etc., which rarely happens. In practice, it is useful to set an appropriate predetermined reference frequency from the perspective of reducing such erroneous determination. On the basis of the result of the determination in Step S17, outputter 160 outputs the dementia information including information to the effect that user A is developing the mild cognitive disorder (transmits the dementia information to notification device 200) (Step S18). When the occurrence frequency of the disordered day does not exceed the predetermined reference frequency in Step S16, outputter 160 does not output the dementia information, but may output dementia information that does not indicate that user A is developing the mild cognitive disorder.

After the process in Step S18 or when the occurrence frequency of the disordered day is discerned in Step S16 as not exceeding the predetermined reference frequency, dementia determination device 100a returns to the process in Step S11. The process in Step S11 is performed, for example, every day.

Dementia determination devices 100b and 100c perform substantially the same operations as dementia determination device 100a described above, and thus, when users A to C develop the mild cognitive disorder, the information to that effect is displayed on the display of notification device 200 installed in management office 21.

Embodiment 2

Dementia information output system 11 which is a partial modification of dementia information output system 10 described in Embodiment 1 will be described below.

Configuration

Dementia information output system 11 includes a dementia determination device obtained by modifying the dementia determination device in dementia information output system 10 (refer to FIG. 2) described in Embodiment 1 and adding a function of outputting dementia information based on the result of discerning whether or not the power supply of an electrical device used by a user is forgotten to be switched OFF (turned OFF). The following description will be given mainly focusing on dementia determination device 1100a which is a modification of dementia determination device 100a for assisted living unit 22a in which user A illustrated in FIG. 2 lives. In dementia information output system 11, dementia determination devices 100b and 100c also have modified configurations similar to dementia determination device 1100a. Features of dementia information output system 11 according to the present embodiment which are not described herein are substantially the same as those of dementia information output system 10 described in Embodiment 1; the same elements are assigned the same reference marks as those assigned in Embodiment 1, and as such explanations thereof will be omitted.

In terms of hardware elements, dementia determination device 1100a is substantially the same as dementia determination device 100a described in Embodiment 1.

Figure 9:
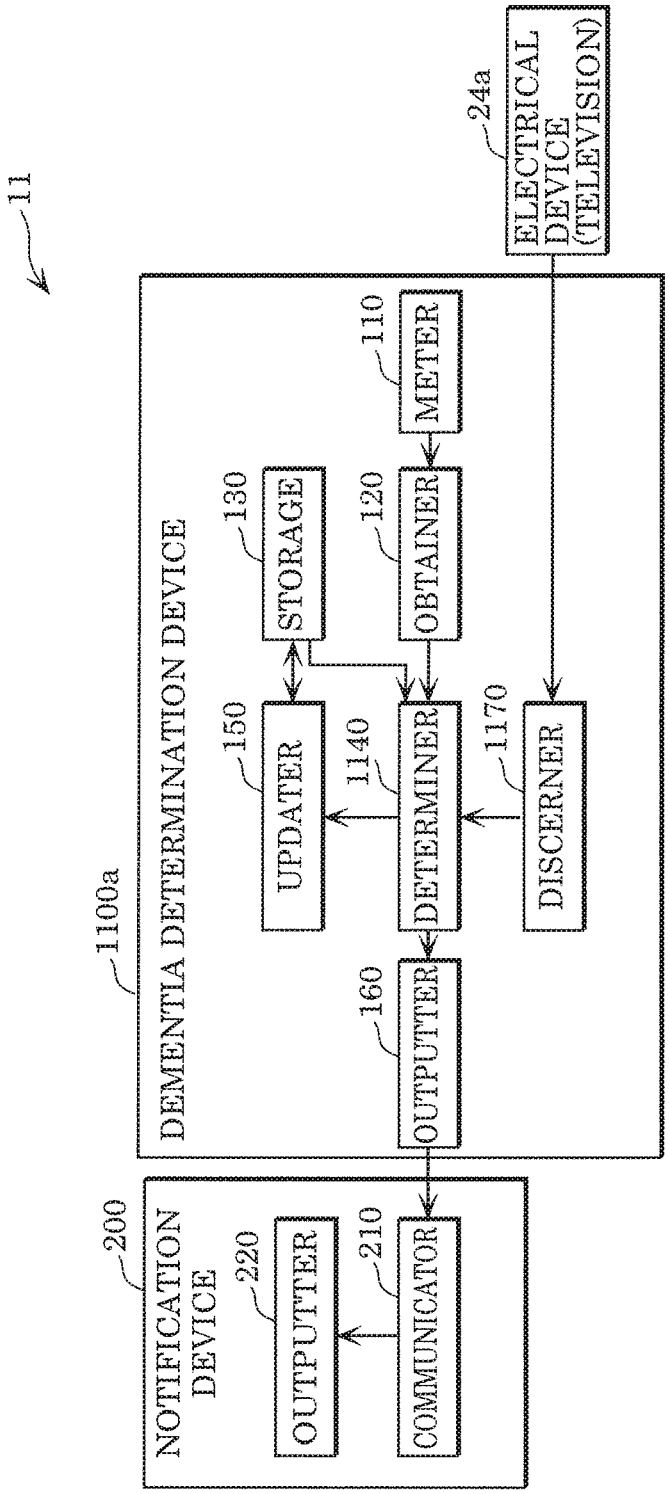
FIG. 9 is a function block diagram of a dementia determination device, etc., according to Embodiment 2.

FIG. 9 is a function block diagram of dementia determination device 1100a in dementia information output system 11 according to the present embodiment. Dementia determination device 1100a is installed in assisted living unit 22a in which user A lives. In this figure, electrical device (television) 24a which is installed in assisted living unit 22a and used by user A and notification device 200 installed in management office 21 are additionally illustrated.

Dementia determination device 1100a has a function of outputting the dementia information on the basis of the result of measuring body motion of user A and information on whether or not user A has forgotten to switch OFF the power supply of the electrical device, and thus includes, as functional elements, meter 110, obtainer 120, storage 130, determiner 1140, updater 150, outputter 160, and discerner 1170, as illustrated in FIG. 9.

Discerner 11170 is implemented, for example, by memory 102, communication I/F 103, and processor 104 which executes the control program. Discerner 1170 has a function of discerning whether or not television 24a is in a power-on state and holding the discerning result in association with time. The power-on state is a state in which the power supply has not been switched OFF and is specifically a state in which power consumption is greater than a predetermined value (for example, zero, a value of approximately zero, a value of standby power, or the like). When the power supply of the electrical device is switched OFF, the electrical device is placed in the power-off state. Discerner 1170 can perform this discerning operation, for example, by obtaining, from television 24a, a signal indicating that television 24a is to be placed in the power-off state or the power-on state immediately after the start of the power-on state and immediately before the start of the power-off state. Furthermore, discerner 1170 may calculate the power consumption of television 24a by obtaining a signal indicating an electric current detected by an electric current sensor provided on a branch circuit, etc., of a distribution panel to which television 24a is connected. In this case, discerner 1170 can discern that the electrical device is in the power-off state when the calculated power consumption is zero or not greater than predetermined standby power (for example, a few watts) and discern that the electrical device is in the power-on state otherwise.

Determiner 1140 has the following function in addition to the functions of determiner 140 described in Embodiment 1. In detail, determiner 1140 has a function of determining whether or not user A is developing the mild cognitive disorder on the basis of whether or not discerner 1170 discerns that electrical device (television) 24a is in the power-on state in the sleep time period of user A specified by obtainer 120 and the occurrence frequency of the day (unit period) in which the magnitude of the difference between the reference data and the measurement result (the amount of body motion of user A in the sleep time period of one day) obtained by obtainer 120 exceeds the predetermined threshold value. Specifically, for example, when the occurrence frequency of the day (the disordered day) in which the absolute value of the difference between the reference data and the amount of body motion of user A in the sleep time period of one day exceeds threshold value σ exceeds the predetermined reference frequency and when discerner 1170 discerns that television 24a is in the power-on state in the sleep time period (for example, at the sleep onset time) of user A, determiner 1140 determines that user A is developing the mild cognitive disorder.

Operations

Operations of dementia determination device 1100a in dementia information output system 11 including the above-described configuration will be described below.

Figure 10:
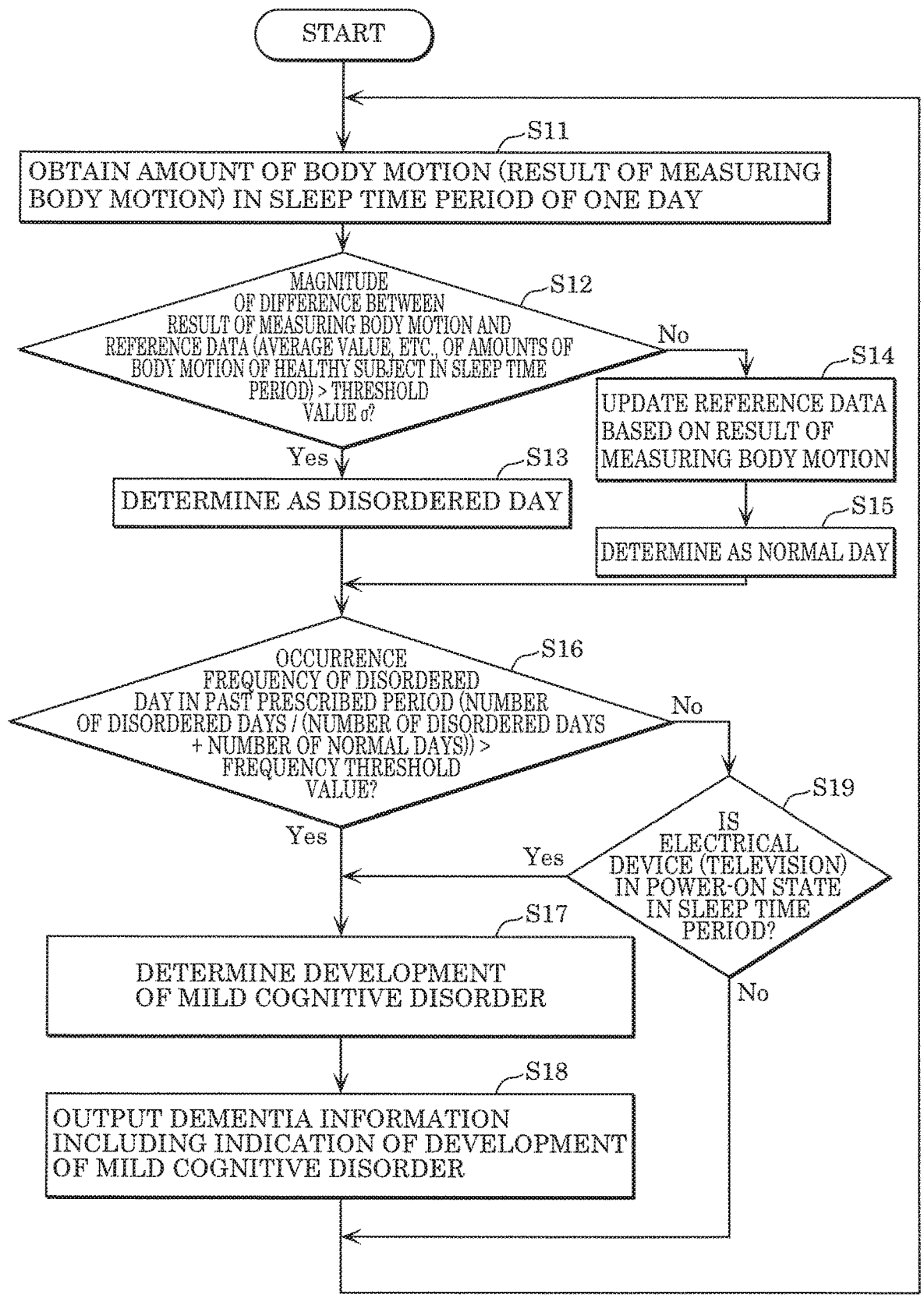
FIG. 10 is a flowchart illustrating a dementia information output process in a dementia determination device according to Embodiment 2.

FIG. 10 is a flowchart illustrating a dementia information output process in dementia determination device 1100a according to the present embodiment. The dementia information output process will be described below with reference to this figure. In this figure, steps that are substantially the same as the process (steps) described in Embodiment 1 are assigned the same reference marks as those in FIG. 8, and as such explanations thereof will be omitted.

Dementia determination device 1100a measures the body motion of user A by meter 110, specifies the sleep time period of user A in one day by obtainer 120, and obtains the result of measuring the body motion (the amount of body motion) in the sleep time period (Step S11).

Determiner 1140 in dementia determination device 1100a determines whether or not the magnitude (absolute value) of the difference between the result of measuring the body motion of user A in the sleep time period of one day which is obtained in Step S11 and the reference data stored in storage 130 exceeds threshold value σ (Step S12). When the magnitude of the difference exceeds threshold value σ, determiner 1140 determines that the day is a disordered day (Step S13). When the magnitude of the difference does not exceed threshold value σ, determiner 1140 causes updater 150 to update the reference data (Step S14), and determines that the day is a normal day (Step S15).

Subsequently, determiner 1140 discerns whether or not the occurrence frequency of the disordered day in the past prescribed period exceeds the frequency threshold value (predetermined reference frequency) (Step S16). When the occurrence frequency of the disordered day exceeds the predetermined reference frequency, determiner 1140 determines that user A is developing the mild cognitive disorder (Step S17). Even in the case where the occurrence frequency of the disordered day does not exceed the predetermined reference frequency, when the state of television 24a discerned by discerner 1170 in the sleep time period (for example, at the sleep onset time) specified in Step S11 is the power-on state (Step S19), determiner 1140 determines that user A is developing the mild cognitive disorder (Step S17). Following the determination in Step S17, outputter 160 outputs the dementia information including information to the effect that user A is developing the mild cognitive disorder (transmits the dementia information to notification device 200) (Step S18).

After the process in Step S18 or when the state of television 24a discerned by discerner 1170 in the sleep time period is the power-on state in Step S19, dementia determination device 1100a returns to the process in Step S11. The process in Step S11 is performed, for example, every day.

With such a dementia information output process, also when user A has forgotten to switch OFF an electrical device (such as a television) at the sleep onset time, etc., the dementia information based on that is displayed on the display of notification device 200.

Other Embodiments, Etc.

Although dementia information output systems 10 and 11 have been described above according to Embodiments 1 and 2, the above-described embodiments are mere examples; it goes without saying that various changes, additions, omissions, and so on can be made.

The above-described embodiments show an example in which dementia information output systems 10 and 11 are used in a nursing care facility, but this is merely one example. For example, dementia information output systems 10 and 11 can be used in a house (such as independent housing or an individual dwelling unit in a housing complex), an elderly housing complex, a hospital, and other facilities.

Figure 11:
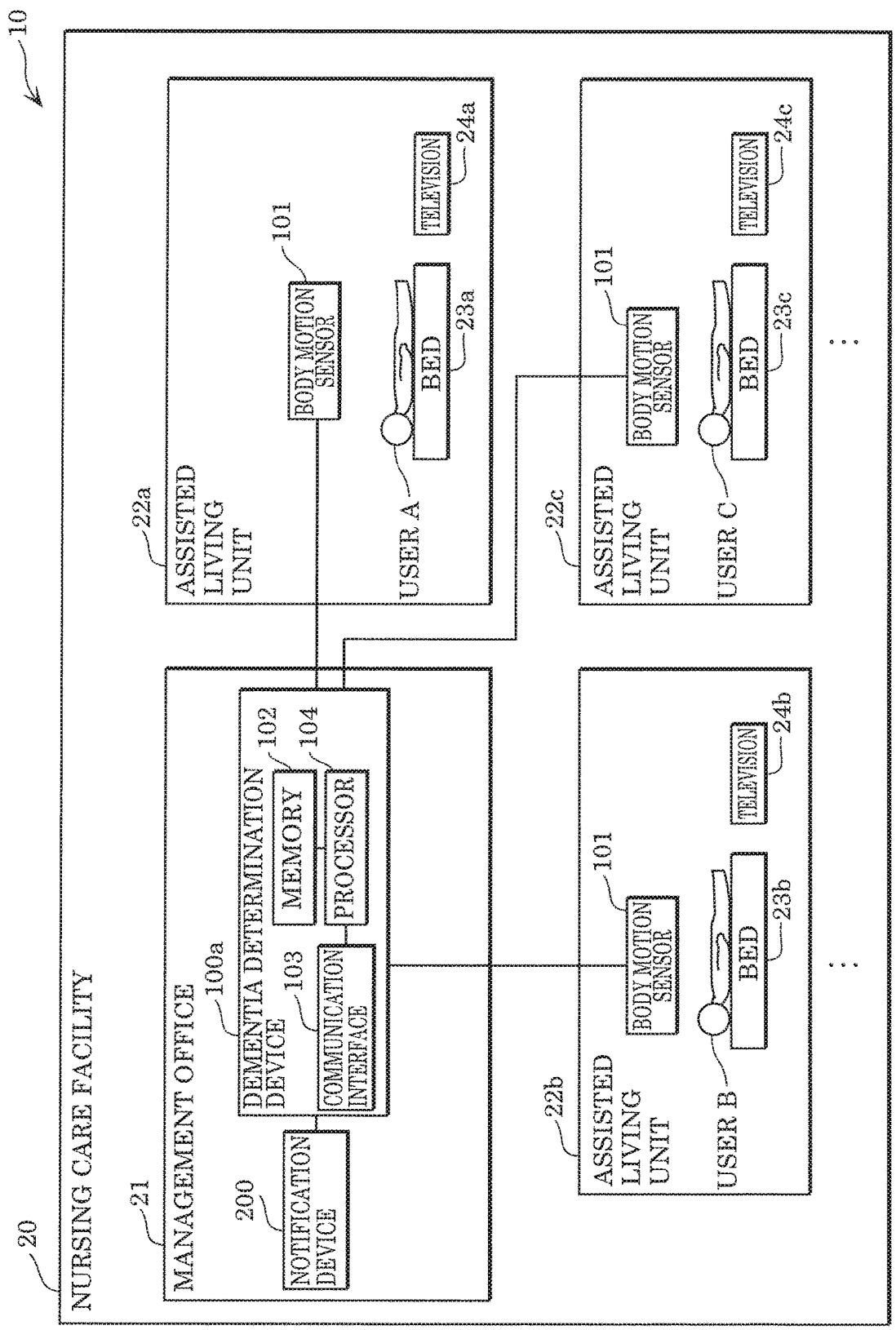
FIG. 11 is a schematic configuration view illustrating an example of a configuration of dementia information output system according to another embodiment.

In the case where dementia determination device 100a in dementia information output system 10 described in the above-described embodiment includes a presentation device (display device) such as a display, dementia determination device 100a except for body motion sensor 101 may be provided in management office 21. In this case, dementia determination device 100a can obtain the results of measuring the body amounts of users from body motion sensors 101 installed in assisted living units 22a to 22c, and, for example, determine, on the basis of the measurement results, whether or not the users are developing the mild cognitive disorder, and output (present) dementia information including the determination results. Note that in the case where dementia determination device 100a is included in management office 21, dementia determination device 100a does not need to include the display device and may transmit the dementia information to notification device 200 in management office 21 and cause notification device 200 to present the dementia information. FIG. 11 illustrates an example of the configuration in which dementia determination device 100a is installed in management office 21.

In the case where dementia information output system 10 outputs information related to the mild cognitive disorder for only one user A, it is sufficient that single dementia determination device 100a be provided.

Furthermore, the destination to which outputter 160 in dementia determination devices 100a and 1100a described above transmits the dementia information is not limited to notification device 200 installed in management office 21. Communication I/F 103 in dementia determination devices 100a and 1100a may be connectable, for example, to a wide area network such as a telephone network and the Internet. Notification device 200 may be a communication device such as a personal computer (PC) provided in a location different from management office 21 or may be an information communication terminal, etc., such as a smartphone, which is a mobile object. For example, it is useful if dementia determination device 100a is installed in a house of an elderly person living alone and an e-mail address, etc., of a smartphone of a family member living away from the elderly person is stored into dementia determination device 100a so that outputter 160 outputs the dementia information to the smartphone. Furthermore, dementia determination devices 100a and 1100a may transmit the dementia information to two or more destinations.

Furthermore, although the above embodiment describes an example in which dementia determination device 100a includes body motion sensor 101, dementia determination device 100a does not need to include body motion sensor 101; it is sufficient that the result of measuring the body motion of the user in the sleep time period can be obtained from body motion sensor 101. In the case of a configuration in which dementia determination device 100a and body motion sensor 101 are separated, body motion sensor 101 may include the functions of meter 110 and obtainer 120, for example. The allocation of the functions between the respective functional elements in dementia determination device 100a is merely one example; for example, obtainer 120 may include meter 110, and, for example, outputter 160 may include determiner 140.

In Embodiment 2, when television 24a is in the power-on state in the sleep time period (for example, at the sleep onset time), determiner 1140 in dementia determination device 1100a determines that user A is developing the mild cognitive disorder. This is merely one example in which development of the mild cognitive disorder is determined on the basis of the power-on state of the electrical device in the sleep time period of user A. For example, it may be possible to determine that user A is developing the mild cognitive disorder when the occurrence frequency of a day in which television 24a is in the power-on state in the sleep time period of user A exceeds a prescribed frequency (for example, twice a week). As another example, it may be possible to determine that user A is developing the mild cognitive disorder on the basis of judgement on prescribed conditions related to combinations of the power-on state of the electrical device in the sleep time period of user A and the occurrence frequency of the disordered day. Television 24a is merely one example of the electrical device which the user uses; the electrical device is not limited to television 24a and may be other devices such as a lighting fixture and audio equipment. Furthermore, dementia determination device 1100a may additionally have a function of discerning, by a sensor or the like, whether a water faucet (water tap) which user A uses is ON or OFF, and when the water faucet is ON in the sleep time period of user A, determining that user A is developing the mild cognitive disorder. Since it is said that when a person develops dementia, what is called "forgetfulness" occurs including forgetting to turn OFF an electrical device and forgetting to turn off a water tap, dementia determination device 1100a can support the "forgetfulness" and appropriately determine the likelihood that user A may be developing the mild cognitive disorder.

Furthermore, although the above-described embodiment suggests that outputter 160 may display the dementia information on the display, the dementia information may be presented in a method other than displaying. Here, presenting the information means outputting the information in such a way that the information is recognized by the five senses of a human being. Examples of the presentation method other than displaying include reproducing speech about the details of the dementia information (speech output from a speaker, etc.) or emitting light and activating a buzzer to inform that the dementia information indicates development of the mild cognitive disorder.

Furthermore, the execution sequence of the processing flow in dementia determination devices 100a and 1100a, etc., described above (for example, the flows illustrated in FIG. 8 and FIG. 10) is not necessarily limited to the above-described sequence; so long as it does not depart from the scope of the invention, the execution sequence may be rearranged or may be partially omitted. Moreover, the entire or part of the processing flow (for example, the flows illustrated in FIG. 8 and FIG. 10) may be executed via hardware or may be executed via software. Note that the processing via software is executed by the processor included in dementia determination devices 100a and 1100a, etc., executing the control program stored in the memory. Furthermore, the control program may be recorded on a recording medium and be distributed or circulated. For example, by installing the distributed control program on the dementia determination device (computer) and causing the processor to execute the control program, it is possible to cause the computer to execute the entire or part of the processing flow illustrated in FIG. 8 and FIG. 10.

Furthermore, forms realized by arbitrarily combining the structural elements and functions described in the above embodiments are included within the scope of the present invention.

Note that various general or specific aspects of the present invention include one or a combination of, for example, device, system, and method.

The configuration, modified aspect, advantageous effect, etc., of the dementia information output system according to an aspect of the present invention will be described below.

(1) Dementia information output systems 10 and 11 according to an aspect of the present invention includes: obtainer 120 which obtains, on a per unit period (for example, 24 hours) basis, the result of measuring body motion (the amount of body motion) of user A in a sleep time period; and outputter 160 (or outputter 220) which outputs dementia information indicating the likelihood that user A is developing a mild cognitive disorder (for example, the mild dementia or the mild cognitive impairment) based on the occurrence frequency of a unit period (for example, the disordered day) in which the magnitude (for example, the absolute value) of a difference (for example, a difference or ratio) between the reference data on the body motion of a healthy subject (for example, user A in the state of being healthy and normal or another healthy subject) in a sleep time period and the result of measuring obtained by obtainer 120 exceeds a predetermined threshold value (for example, threshold value σ). The information of the mild cognitive disorder may indicate the result of determining whether or not the user is developing the mild cognitive disorder, may be an index value, etc., indicating the level of likelihood of development of the mild cognitive disorder, or may include both of these.

This dementia information output systems 10 and 11 are capable of outputting dementia information indicating the likelihood of development of the mild cognitive disorder without the need to set a rule such as a switch operation. With this, it is possible to recognize the likelihood that user A is developing the mild cognitive disorder by checking the output dementia information.

(2) For example, the reference data may be the result of measuring the body motion of user A in the sleep time period at the time when user A is a healthy subject.

In this case, the result of measuring the body motion of user A in the sleep time period and the reference data which are to be compared in order to obtain the magnitude of the difference are generally the same except for the time at which the measurement is conducted. Thus, it is possible to output the dementia information that relatively accurately indicates the likelihood of development of the mild cognitive disorder.

(3) For example, the unit period may be 24 hours in length, dementia information output systems 10 and 11 may further include determiners 140 and 1140 which, when the occurrence frequency of the unit period in which the magnitude of the difference between the reference data and the result of measuring obtained by obtainer 120 exceeds the predetermined threshold value exceeds a predetermined reference frequency (for example, a frequency of 70% of a period not less than the past one week), determines that user A is developing the mild cognitive disorder, and when determiners 140 and 1140 determine that user A is developing the mild cognitive disorder, outputter 160 outputs the dementia information indicating that user A is developing the mild cognitive disorder.

Thus, it is possible to recognize that user A is developing the mild cognitive disorder by checking the output dementia information. For example, people concerned, caretakers, etc., for user A do not need to stay close to observe user A, but can recognize, by the dementia information output by dementia information output systems 10 and 11 (notification device 200, etc.), that user A develops the mild cognitive disorder. With recognition of development of the mild cognitive disorder from the dementia information as a trigger, for example, a doctor can fully examine the condition of user A and provide appropriate treatment, etc. At the time of this examination, the condition of the body (brain, etc.) of user A is checked with various measuring instruments (computed tomography (CT) scanner, etc.) as necessary. In this manner, dementia information output systems 10 and 11 produce the advantageous effect of outputting the dementia information which can be used as a trigger for conducting an examination or a test using an instrument, for example.

(4) For example, dementia information output systems 10 and 11 may further include updater 150 which updates the reference data to reflect the result of measuring in the unit period in which the magnitude of the difference between the reference data and the result of measuring (the amount of body motion of user A in the sleep time period) obtained by obtainer 120 does not exceed the predetermined threshold value, and when the occurrence frequency of the unit period in which the magnitude of the difference between the reference data updated by updater 150 and the result of measuring obtained by obtainer 120 after the update exceeds the predetermined threshold value exceeds the predetermined reference frequency, determiners 140 and 1140 may determine that user A is developing the mild cognitive disorder.

With this, the reference data is updated by reflecting the result of measuring the body motion of user A in the sleep time period, and thus it is possible to accurately determine development of the mild cognitive disorder by determiners 140 and 1140 in accordance with the individual circumstance (for example, the trend of the amount of body motion) of user A.

(5) For example, dementia information output systems 10 and 11 may further include meter 110 which measures body motion of user A, and obtainer 120 may specify a sleep time period of user A based on the result of measuring the body motion of user A by meter 110, and obtain the result of measuring in the sleep time period that has been specified. Note that dementia information output systems 10 and 11 can specify, as the sleep time period, the period of time between the sleep onset time and the time of awakening which is identified based on the result of measuring the body motion, for example.

With this, it is possible to deal with the circumstance of user A, compared to the case in which the sleep time period is fixedly set to the period of time between 23 o'clock and 6 o'clock, for example, and thus development of the mild cognitive disorder can be accurately determined.

(6) For example, dementia information output system 11 may further include meter 110 which measures body motion of user A, and obtainer 120 may specify a sleep time period of user A based on the result of measuring the body motion of user A by meter 110, and obtain the result of measuring in the sleep time period that has been specified, dementia information output system 11 may further include: discerner 1170 which discerns whether or not an electrical device (for example, television 24a) used by user A is in a power-on state; and determiner 1140 which determines whether or not user A is developing the mild cognitive disorder based on whether or not discerner 1170 discerns that the electrical device is in the power-on state in the sleep time period of user A that has been specified by obtainer 120, and the occurrence frequency of the unit period (for example, the disordered day) in which the magnitude of the difference between the reference data and the result of measuring obtained by obtainer 120 exceeds the predetermined threshold value, and when determiner 1140 determines that user A is developing the mild cognitive disorder, outputter 160 (or outputter 220) may output the dementia information indicating that user A is developing the mild cognitive disorder.

With this, development of the mild cognitive disorder is determined on the basis of that fact that user A forgets to switch OFF (forgets to turn OFF) the power supply of the electrical device such as television 24a at the sleep onset time, and thus it is possible to more appropriately determine the development of the mild cognitive disorder.

(7) For example, when the occurrence frequency of the unit period (for example, the disordered day) in which the magnitude of the difference exceeds the predetermined threshold value exceeds the predetermined reference frequency and when the frequency in which discerner 1170 discerns that the electrical device is in the power-on state in the sleep time period of user A exceeds the prescribed frequency, determiner 1140 may determine that user A is developing the mild cognitive disorder. Examples of the prescribed frequency include zero and twice a week.

With this, development of the mild cognitive disorder is determined also on the basis of the frequency in which user A forgets to switch OFF (forgotten to turn OFF) the power supply of the electrical device such as television 24a at the sleep onset time, and thus it is possible to more appropriately determine the development of the mild cognitive disorder.

(8) For example, outputter 160 may output the dementia information by presenting the dementia information.

With this, it is possible to obtain, from dementia information output systems 10 and 11, the dementia information about the likelihood that user A may be developing the mild cognitive disorder.

(9) For example, outputter 160 may output the dementia information by transmitting the dementia information to notification device 200. Notification device 200 may be included in dementia information output systems 10 and 11 or may be located outside dementia information output systems 10 and 11.

With this, it is possible to receive and, for example, display, the dementia information by notification device 200. Thus, using notification device 200 separated from a device (for example, dementia determination devices 100a and 1100a) in dementia information output systems 10 and 11 including meter 110 which measures the body motion of user A, people concerned, caretakers, etc., for user A can obtain the dementia information about user A.

(10) The non-transitory recording medium having the control program recorded thereon according to an aspect of the present invention is for causing a device (dementia determination devices 100a and 1100a) including processor (microprocessor) 104 to execute a dementia information output process including: obtaining, on a per unit period basis, the result of measuring body motion of a user (subject) in the sleep time period (for example, Step S11); and outputting dementia information indicating the likelihood that the user is developing the mild cognitive disorder based on the occurrence frequency of a unit period in which the magnitude of a difference between reference data on body motion of a healthy subject in the sleep time period and the result of measuring obtained exceeds a predetermined threshold value (for example, Steps S12, S13, and S16 to S18).

By installing, on the dementia determination device (computer), the control program recorded on the recording medium, and causing processor 104 to execute the control program, it is possible to output the dementia information indicating the likelihood that the user may be developing the mild cognitive disorder.

The invention claimed is:

1. A dementia information output system, comprising:
an obtainer which obtains, on a per unit period basis, a result of measuring body motion of a user in a sleep time period;
a determiner which determines, by comparing, on the per unit period basis, reference data on body motion of a healthy subject in the sleep time period and the result of measuring obtained by the obtainer, an occurrence frequency of a unit period in which a magnitude of a difference between the reference data and the result of the measuring obtained by the obtainer exceeds a predetermined threshold value, per a prescribed period; and
an outputter which outputs dementia information indicating a likelihood that the user is developing a mild cognitive disorder, the likelihood being based on a determination result of the determiner,
wherein the prescribed period is a period not less than one week,
wherein the unit period is one day, and
wherein the unit period in which the magnitude of the difference between the reference data and the result of the measuring exceeds the predetermined threshold value includes both (i) a first unit period in which the reference data is greater than the result of the measuring by the predetermined threshold value or more and (ii) a second unit period in which the reference data is smaller than the result of the measuring by the predetermined threshold value or more.

2. The dementia information output system according to claim 1,
wherein the reference data is a result of measuring body motion of the user in the sleep time period at a time when the user is the healthy subject.

3. The dementia information output system according to claim 1,
wherein when the occurrence frequency of the unit period in which the magnitude of the difference between the reference data and the result of measuring obtained by the obtainer exceeds the predetermined threshold value exceeds a predetermined reference frequency, the determiner determines that the user is developing the mild cognitive disorder, and
when the determiner determines that the user is developing the mild cognitive disorder, the outputter outputs the dementia information indicating that the user is developing the mild cognitive disorder.

4. The dementia information output system according to claim 3, further comprising:
an updater which updates the reference data to reflect the result of measuring in a unit period in which the magnitude of the difference between the reference data and the result of measuring obtained by the obtainer does not exceed the predetermined threshold value,
wherein when an occurrence frequency of a unit period in which a magnitude of a difference between the reference data updated by the updater and the result of measuring obtained by the obtainer after the update exceeds the predetermined threshold value exceeds the predetermined reference frequency, the determiner determines that the user is developing the mild cognitive disorder.

5. The dementia information output system according to claim 1, further comprising:
a meter which measures body motion of the user,
wherein the obtainer specifies a sleep time period of the user based on a result of measuring the body motion of the user by the meter, and obtains the result of measuring in the sleep time period that has been specified.

6. The dementia information output system according to claim 1, further comprising:
a meter which measures body motion of the user,
wherein the obtainer specifies a sleep time period of the user based on a result of measuring the body motion of the user by the meter, and obtains the result of measuring in the sleep time period that has been specified,
the dementia information output system further comprises:
a discerner which discerns whether or not an electrical device used by the user is in a power-on state; and
a determiner which determines whether or not the user is developing the mild cognitive disorder based on whether or not the discerner discerns that the electrical device is in the power-on state in the sleep time period of the user that has been specified by the obtainer, and the occurrence frequency of the unit period in which the magnitude of the difference between the reference data and the result of measuring obtained by the obtainer exceeds the predetermined threshold value, and
when the determiner determines that the user is developing the mild cognitive disorder, the outputter outputs the dementia information indicating that the user is developing the mild cognitive disorder.

7. The dementia information output system according to claim 6,
wherein when the occurrence frequency of the unit period in which the magnitude of the difference exceeds the predetermined threshold value exceeds the predetermined reference frequency and when a frequency in which the discerner discerns that the electrical device is in the power-on state in the sleep time period of the user exceeds a prescribed frequency, the determiner determines that the user is developing the mild cognitive disorder.

8. The dementia information output system according to claim 1,
wherein the outputter outputs the dementia information by presenting the dementia information.

9. The dementia information output system according to claim 1,
wherein the outputter outputs the dementia information by transmitting the dementia information to a notification device.

10. The dementia information output system according to claim 1,
wherein the determiner determines, as part of determining the occurrence frequency, a total number of consecutive unit periods in which a magnitude of a difference between the reference data and the result of measuring obtained by the obtainer exceeds a predetermined threshold.

11. A non-transitory computer-readable recording medium having a control program recorded thereon for causing a device including a microprocessor to execute a dementia information output process including:
obtaining, on a per unit period basis, a result of measuring body motion of a user in a sleep time period;
determining by comparing, on the per unit period basis, reference data on body motion of a healthy subject in the sleep time period and the result of measuring body motion of the user in the sleep time period, an occurrence frequency of a unit period in which a magnitude of a difference between the reference data and the result of the measuring body motion of the user in the sleep time period exceeds a predetermined threshold value, per a prescribed period; and
outputting dementia information indicating a likelihood that the user is developing a mild cognitive disorder based on a determination result of determining the occurrence,
wherein the prescribed period is a period not less than one week;
wherein the unit period is one day, and
wherein the unit period in which the magnitude of the difference between the reference data and the result of the measuring exceeds the predetermined threshold value includes both (i) a first unit period in which the reference data is greater than the result of the measuring by the predetermined threshold value or more and (ii) a second unit period in which the reference data is smaller than the result of the measuring by the predetermined threshold value or more.

* * * * *